US007435424B1

(12) United States Patent
Copeland et al.

(10) Patent No.: US 7,435,424 B1
(45) Date of Patent: Oct. 14, 2008

(54) HIGH UNSAPONIFIABLES AND METHODS OF USING THE SAME

(75) Inventors: Lee Roy Copeland, Mesa, AZ (US); Robert Kleiman, Mesa, AZ (US); Sambasivarao Koritala, Tempe, AZ (US); James H. Brown, Scottsdale, AZ (US); Melanie K. Cummings, Chandler, AZ (US)

(73) Assignee: International Flora Technologies, Ltd., Chandler, AZ (US)

( * ) Notice: Subject to any disclaimer, the term of this patent is extended or adjusted under 35 U.S.C. 154(b) by 0 days.

(21) Appl. No.: 09/478,071

(22) Filed: Jan. 3, 2000

(51) Int. Cl.
*A01N 25/02* (2006.01)

(52) U.S. Cl. .................. 424/406; 424/400; 424/401; 424/405; 424/776

(58) Field of Classification Search .................. 424/400, 424/401, 405, 406, 485, 195.15, 195.16, 424/195.17, 195.18, 725, 757, 764, 776, 424/780; 514/558, 76–78
See application file for complete search history.

(56) References Cited

U.S. PATENT DOCUMENTS

| 2,240,365 | A | * | 4/1941 | Dreger | 530/208 |
| 5,679,393 | A | | 10/1997 | Laur et al. | 426/417 |
| 5,705,722 | A | * | 1/1998 | Monnier et al. | 585/240 |
| 5,759,555 | A | | 6/1998 | Moy | 424/401 |
| 5,928,659 | A | * | 7/1999 | Moy | 424/401 |

FOREIGN PATENT DOCUMENTS

FR        79 30956        6/1981

OTHER PUBLICATIONS

M.J. Werman et al., A Simple and Sensitive Method for Detecting Avocado Seed Oil in Various Avocado Oils, 1996, 665-667, JAOCS vol. 73, No. 5.
D.P. Schwartz, Improved Method for Quantitating and Obtaining the Unsaponifiable Matter of Fats and Oils, Feb. 1998, 246-251, JAOCS, vol. 65, No. 2.

(Continued)

*Primary Examiner*—Neil Levy
(74) *Attorney, Agent, or Firm*—The Noblitt Group, PLLC

(57) ABSTRACT

Materials with high levels of unsaponifiable matter, such as extracts from plants, result in Hydrolysates with unique properties. The very properties that are sought in the traditional saponification of natural oils are a result of low levels of unsaponifiables. These properties include high levels of aqueous surfactant activity, water-solubility or ready water-dispersability, activity as foaming agents, and the like. The very objective of traditional saponification processes is to increase the water-solubility and surfactant activity of naturally occurring materials. It has been found that the application of a hydrolysis process to materials, particularly materials with a high level of unsaponifiables (e.g., at least 6% by total weight of the material) produces a product with properties significantly different from those products resulting from the conventional saponification of materials with less than 6% by weight of unsaponifiables. The resulting Hydrolysates from the practice of the present invention are substantive, resisting both physical and aqueous-based removal from skin and hair, exhibit a very unique surfactant property, and are not foaming agents with water. Hydrolysates according to the present invention may thus be used to enhance the performance of cosmetics and pharmaceuticals. These Hydrolysates are bioactive agents and alternative natural carrying agents for topical application of materials, particularly for application of materials to the skin or hair of subjects, and provide a substantive support for the materials carried.

12 Claims, 7 Drawing Sheets

OTHER PUBLICATIONS

R.S. Farag et al., The Lipids of Various Fungi Grown on an Artificial Medium, Jul. 1981, 765 et seq., JAOCS.

R.J. Maxwell et al., A Rapid, Quantitative Procedure for Measuring the Unsaponifiable Matter from Animal, Marine, and Plant Oils, Jun. 1979, 634-636, JAOCS, vol. 56, No. 6.

R.J. Maxwell et al., Determination of the Upsaponifiable Matter in Fatty Acids by a Rapid Column Method, Nov. 1981, 1002-1004, JAOCS.

V. Paganuzzi et al., On the Composition of Iranian Olive Oil, Dec. 1979, 925 et seq., JAOCS vol. 56, No. 12.

M. Bastic et al., Hydrocarbons and Other Weakly Polar Unsaponifiables in Some Vegetable Oils, Dec. 1978, 886 et seq., JAOCS.

P. Nichols, Marine oils from Australian fish: characterization and value added products, Dec. 20, 1999, 1-4, http://www.frdc.com.au/ub/reports/id/94-115.htm.

R. Barnaby, Sea Grant News and Notes from Around the Nation "Roughy not so fat after all", Dec. 20, 1999, 1-3, http://www..seagrantnews.org/news/tips/tips_oct95.htm.

Ultrahydrophytosqualene: New Processes for the Generation of Squalene by Supercritical Fluid Extraction from Waste of Olive Oil Production and Hydrogenation of Squalene, Dec. 20, 1999, 1-4, http://www.nf-2000.org/secure/fair/f348.htm.

* cited by examiner

Fig. 1 Keri Lotion Nova Meter Study

Fig. 3  Average Percent Reduction

Fig. 4 Aquapel, Horse 1

*Per Dr. McPhaul: Horse 1 is a dark brown horse, which means that he had to get closer to see the flies, which means that the flies didn't cooperate during the counting process.*

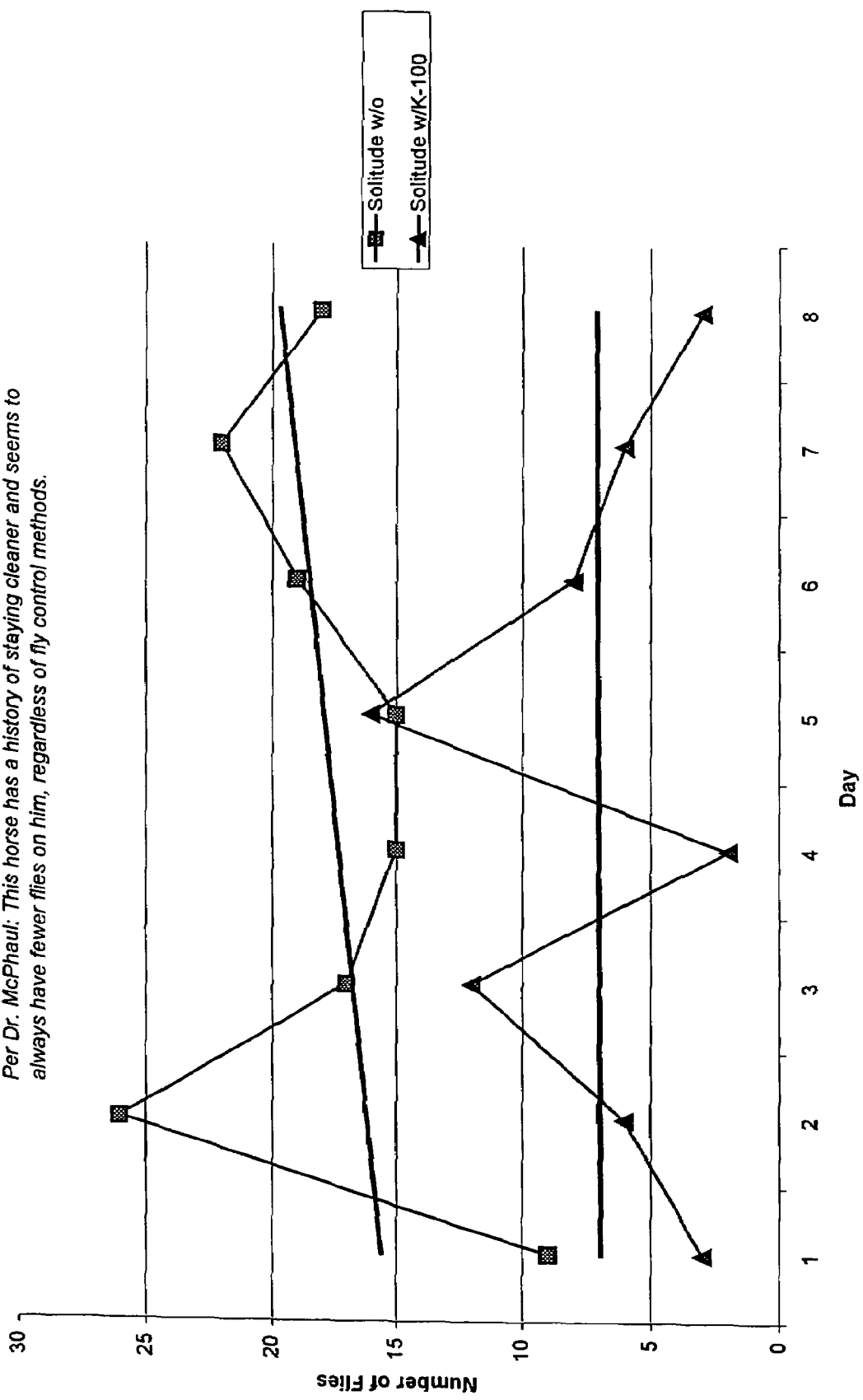

HIGH UNSAPONIFIABLES AND METHODS OF USING THE SAME

FIELD OF THE INVENTION

The present invention relates to a novel composition of matter derived from natural materials or extracts of natural materials. In particular the invention relates to substantive carriers derived from natural waxes, oils, and extracts, and in particular to substantive carriers derived from natural ingredients with relatively high levels of unsaponifiable materials (as defined below) and methods of using the same.

BACKGROUND OF THE INVENTION

Vegetable and animal fats are organic lipid materials that generally contain esters of long-chain fatty acids and glycerine. Under certain conditions these esters react with water (hydrolysis) form an alcohol (glycerine) and fatty acids. (Hydrolysis is the splitting of a compound into components by the addition of water and an enzyme, acid or base.) The results of a hydrolysis reaction are known as "Hydrolysates". When heated in the presence of an alkali hydroxide the above mentioned esters yield soap (the alkali salt of the fatty acid) and glycerine; this particular hydrolysis process is called saponification. "Saponification" and "saponifying" are used herein in their normal manner to mean the hydrolysis reaction between a wax, oil or fat with an alkali metal or alkaline earth metal hydroxide to form the corresponding metallic salt soap. These fats and oils have a saponification value that is the number of milligrams of potassium hydroxide required for complete saponification of one gram of free organic acid and/or organic acid ester.

The post saponification products may either be hydrophilic (water soluble) or hydrophobic (water insoluble). Herein we will use the term "unsaponifiable" to mean those materials that, after the saponification reaction is completed, remain water insoluble. This is in full accord with the A.O.C.S. Official Method Ca 6b-53, which defines unsaponifiable materials as those substances frequently found as components of fats and oils, which cannot be saponified by the usual caustic treatment, but which are soluble in ordinary fats and oils. Included, but not limiting, in the group of unsaponafiable materials are higher aliphatic alcohols, sterols, pigments, mineral oils, and hydrocarbons. Unsaponifiable materials are generally non-volatile at 103° C. The weight percent of unsaponifiable material in a substance may be measured directly by measuring the weight percent of those materials defined as unsaponifiable.

The most well known vegetable and animal lipids have low levels, less than five percent (<5%), of unsaponifiable materials. This means that most of the products of the saponification reaction are water-soluble. Commonly used vegetable oils have levels of unsaponifiable materials generally below 1%. For example, saponification of soybean oil leaves 0.7 weight percent unsaponifiable materials, saponification of olive oil leaves 1.2 weight percent unsaponifiable materials, and saponification of peanut oil leaves 0.4 weight percent unsaponifiable materials. However, some commercial oils contain higher concentrations of unsaponifiable products, up to as much as 6.0 weight percent unsaponifiable materials. Examples include: crude rice bran oil, 4.2% unsaponifiables, crude wheat germ oil, 6% unsaponifiables, and shea butter, 9-13% unsaponifiables. Materials with high levels of unsaponifiables, such as shea butter, are not a preferred starting material for the production of soap because of the high amount of unsaponifiable materials left after the saponification reaction.

In most cases, the hydrolysis products of a saponification process are used solely for a single purpose, which is as a hygienic skin-cleansing agent (soap). In the past, the basic ingredient of soap was animal fat (also known as lard or tallow) with wood ash based lye used in the saponification process. Ideally a bar of soap has a suitable hardness to maximize user cycles and has a certain amount of resistance to water reabsorption when not in use, while at the same time providing sufficient lather (acting as a foaming agent) to enhance the cleaning ability of the soap. Animal lipids as the active ingredient in the soap making process will generally meet these user demands to a greater or lesser degree. Current soap production continues to rely heavily on animal fats in their products to meet consumer demand and production requirements, although more and different types of synthetic materials are beginning to find use in soap compositions. The various synthetic compounds and mixtures of compounds have become very popular additions in modern soap making technology for their improvement to soap quality and user satisfaction. However, these synthetic based soaps are generally resistant to the natural breakdown processes (i.e. biodegradability) and are thus relatively persistent in the environment.

There are basically two distinct types of soap manufacturing processes. In a first method, oils and fats are boiled in an open kettle with caustic alkali solutions, bringing about saponification gradually until all of the fats and oils are completely saponified, followed by the removal of the glycerine. This process may either run in batch or in a continuous process.

In a second method, which is typically a continuous method (but may be run in batch form), fatty acids and alkali are brought together in proper portions for complete saponification in a mixing valve or other device which brings them in intimate contact. The progress of saponification depends on the temperature, time of contact and efficiency of mixing. Concentrated solutions produced by these methods are referred to as "neat" soaps, and possess a concentration of 60-65% soap, about 35% water and traces of salt and glycerine. It is from this product that consumer soaps in the form of bars, flakes, granules and powders are produced, by first drying the neat soap into pellets having a moisture content of about, 12-16% followed by finishing steps, such as milling, plodding, amalgamating, and the like.

Consumer bar soaps today are manufactured from coconut oil and/or tallow or their fatty acids. Palm kernel oil is sometimes substituted for coconut oil for economic reasons, and soaps prepared with palm kernel oil are adjusted for performance characteristics similar to non-substituted tallow/coconut formulations. Palm oil is also often substituted for tallow.

A consideration in selecting materials for making soap is the proper ratio of saturated versus unsaturated, and long-versus-short-chain fatty acids that result in a soap having the desired qualities of stability, solubility, ease of lathering, hardness, cleaning ability, and the like. It has been determined that soaps prepared from fatty acid mixtures wherein a majority of the fatty acids in the mixtures has carbon chains less than twelve atoms irritate skin. Soaps prepared from saturated $C_{16}$ and $C_{18}$ fatty acids are typically too insoluble for consumer use. Thus, the preferred materials for soap production have fatty acid chains between twelve and eighteen carbon atoms in length.

Saponification of tallow produces a soap comprised of a mixture of fatty acids of $C_{14:0}$, $C_{16:0}$, $C_{18:0}$, and $C_{18:0}$ (myristic, palmitic, stearic and oleic acids, respectively) and saponification of coconut oil produces a soap comprised of a mixture of fatty acids of $C_{12:0}$ and $C_{14:0}$ (lauric acid and myristic acid, respectively) and significant amounts of $C_{8:0}$ and $C_{10:0}$ fatty acids. Consumer soap preparations usually contain tallow/coconut (T/C) ratio ranges from approximately 90:10 to 75:25. Since lauric acid is found only in the coconut fraction of T/C mixtures, the most dramatic change observed in increasing the percent of the coconut fraction of T/C mixtures is the increase in the lauric acid. Increasing the coconut fraction in T/C fatty acid containing soaps generally improves the desirable foaming characteristics of such soaps. However, in soaps with T/C ratios of 50:50, the desirable skin mildness properties are reduced.

Typical fatty acid distribution (in weight percent) of the main soap making components is given below:

| Carbon Chain Length | Tallow | Palm | Coconut | Palm Kernel |
|---|---|---|---|---|
| 10:0 (capric) | 0.1 | 0.0 | 15.1 | 6.4 |
| 12:0 (lauric) | 0.1 | 0.3 | 48.0 | 46.7 |
| 14:0 (myristic) | 2.8 | 1.3 | 17.5 | 16.2 |
| 16:0 (palmitic) | 24.9 | 47.0 | 9.0 | 8.6 |
| 18:0 (stearic) | 20.4 | 4.5 | 9.0 | 8.6 |
| 18:1 (oleic) | 43.6 | 36.1 | 5.7 | 16.1 |
| 18:2 (linoleic) | 4.7 | 9.9 | 2.6 | 2.9 |
| 18:3 (linolenic) | 1.4 | 0.2 | 0.0 | 0.0 |
| 20:0 (arachidic) | 1.8 | 0.3 | 0.0 | 0.4 |

From the table it can be seen that the coconut and palm kernel fats (both known as the lauric fats) are particularly rich in the $C_{10-14}$ saturated fatty acids, particularly derivatives from lauric acid itself. Another fat that contains saturated, relatively short chain fatty acids similar to coconut oil is babassu oil. In contrast, tallow and palm oil per se are industrial sources of non-lauric fats, especially those containing $C_{16}$ and $C_{18}$ fatty acids.

In general the longer chain fatty acid alkali salts, particularly the less expensive $C_{16}$ and $C_{18}$ salts (as obtained from tallow and palm oils), provide structure in the finished soap bars and prevent or retard disintegration of the soap bar on exposure to water. The more expensive, shorter chain, lauric fat-derived, (i.e., lauric acid salts) and other soluble salts (typically as obtained from coconut and palm kernel oil) contribute to the lathering properties of the overall composition. A general problem in the formulation of bar soaps has been finding a balance between providing structure (generally obtained from the long chain component) and maintaining lathering properties (generally obtained from the more expensive short chain component) at a practical overall cost.

In addition to fatty acid salts, soap bars can contain free fatty acids. The addition of free fatty acids is known as 'superfatting'. Superfatting at a 5-10% free fatty acids level is known to give a copious, creamy lather. Other superfatting agents used include citric and other acids that function by promoting the formation of free fatty acids in the fat blend.

For the manufacture of the soap cakes, common additives can be added to the base soap in the normal quantities, referred to 100 parts by weight of base soap, such as overgreasing agents (1 to 3 wt. %), stabilizers (antioxidants, complexing agents) (0.05 to 0.5 wt. %), perfume (0.5 to 3 wt. %) and possibly dyes (0.05 to 0.3 wt. %) as well as skin protection agents such as sorbitol, glycerine or the like (1 to 5 wt. %).

The pharmaceutical and cosmetic industries have been using fat extracts of vegetable origin since earliest times. A number of years ago it became apparent in these industries that particularly valuable biological properties resulted from the use of vegetable fats or extracts of vegetable fats rich in unsaponifiable materials. Certain vegetable oils, for example avocado, and, in particular, shea butter, are known to be particularly rich in unsaponifiable materials and/or to contain, these unsaponifiable materials.

A process for enriching unsaponifiables in oils, especially shea butter, for use in cosmetic and pharmaceutical compositions is described in U.S. Pat. No. 5,679,393, issued to Laur. This process concentrates the unsaponifiable fraction of fats and oils by the processes of crystallization and fractionation. This method is expensive and it does not liberate the alcohol moiety from the starting compounds (hydrolysis). Thus, the Laur process and methods for use of the products thereof never utilize hydrolysis to create alkali salts and liberate alcohols and other unsaponifiables.

Hydrolysates applied topically to animate and inanimate objects find use in numerous non-cleansing areas ranging from cosmetic preparations, pharmaceuticals, hydration formulations, insecticides, insect repellant, and the like. One of the areas of interest created by the varied uses of topically applied agents is maximizing the duration a topically applied active agent is present on the applied surface (substantivity). As a result of this intense interest, the search for ways to improve the duration of a fixed amount of topically applied cosmetics, pharmaceuticals, and bioactive agents has been of prime importance in all areas wherein topically applied cosmetics, pharmaceuticals, and bioactive agents are employed. An example of this interest may be found in the prior art relating to sunscreen compositions.

The use of sunscreen compositions is required by a large segment of society since only a small portion of those exposed to sunlight have the natural pigmentation which provides protection against the harmful effects of solar radiation. Because many people show erythema under even short exposures to sunlight, there is a need for sunscreen compositions that protect against erythema-causing radiation, i.e., ultraviolet radiation, so that longer exposure to the sunlight with less risk of sunburn is possible.

A variety of sunscreen compositions are known in the art. One tendency in formulating sunscreen compositions has been to prepare compositions that are water-resistant to the skin. One method is to chemically modify the ultraviolet absorber to increase its interaction with the skin by quaternizing imidazoles, as described in U.S. Pat. No. 3,506,758; another method is to copolymerize ultraviolet light absorbing monomers with other monomers to form water-resistant films, as described in U.S. Pat. Nos. 3,529,055 and 3,864,473; yet another method is to form polymeric films with water-insoluble polymers, as described in U.S. Pat. No. 3,784,488.

The use of the acid form of crosslinked ethylene-maleic anhydride copolymers to retain ultraviolet light absorbers is disclosed in U.S. Pat. No. 3,821,363. The use of water insoluble acrylate polymer having a solubility parameter of 6 to 10 in weak hydrogen bonding solvents is disclosed in U.S. Pat. No. 4,172,122. The use of water-insoluble, alcohol-soluble, film-forming poly-amide materials is disclosed in U.S. Pat. No. 3,895,104 solely for the purpose of providing improved substantivity.

The cosmetics and other applications of the prior art have not heretofore utilized the substantivity inherent in Hydrolysates of naturally derived materials containing high unsaponifiables or long chain esters (greater than 18 carbons in length) to enhance the intrinsic substantivity of topically applied agents with which they are incorporated. Previously, the purpose of employing polymers or polymeric materials in the compositions of the prior art has been directed towards improving the adherency, i.e., substantivity, of the topical material to the skin or have been employed solely as thickening agents. The improved substantivity, among other properties, achieved by employing the Hydrolysates according to the present invention has not heretofore been disclosed or appreciated in the prior art.

The increased substantivity of topically applied agents provides for more effective and economical use of such materials. In particular, the present invention provides improved compositions, including emollients, skin hydrating agents, sunscreens, lipsticks, make up, insect repellants, insecticides, pesticides, herbicides, and the like, having at least an effective amount of a Hydrolysate including high levels of unsaponifiable materials, preferably of long chain esters.

SUMMARY OF THE INVENTION

The hydrolysis of materials with high levels of unsaponifiable matter, such as extracts from plants, result in products with unique properties. Traditional products of saponification of natural oils function as they do as a direct result of the low level of unsaponifiable contained therein (as discussed above). Such properties include high levels of aqueous surfactant activity, water-solubility or ready water-dispersability, activity as foaming agents, and the like. The very objective of traditional saponification processes is to increase the water-solubility and surfactant activity of naturally occurring materials. It has been found that the application of hydrolysis to materials, particularly naturally derived materials, with a high unsaponifiables fraction (e.g., at least 6% by total weight of the material) in combination with a saponifiable fraction produces a Hydrolysate with properties that are significantly different from those products resulting from the conventional saponification of materials with less than 6% by weight of unsaponifiable.

The resulting products from the practice of the present invention are substantive, water resistant, prevent unwanted absorption of a carried active ingredient by the applied surface, exhibit a unique surfactant functionality, and are not foaming agents with water. Some unexpected uses for the resulting Hydrolysates have been found to be as an emollient and/or an alternative natural carrying agent for topical application of cosmetics, pharmaceuticals, and bioactive agents, particularly to the skin of subjects, and provide a substantive support for the materials carried.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Detailed Description of the Invention is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. § 112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DESCRIPTION OF THE DRAWINGS

FIG. 7 is the graph of the fly reduction for Solitude when incorporating the Hydrolysates of the present invention.

DETAILED DESCRIPTION OF THE INVENTION

Figure 1:
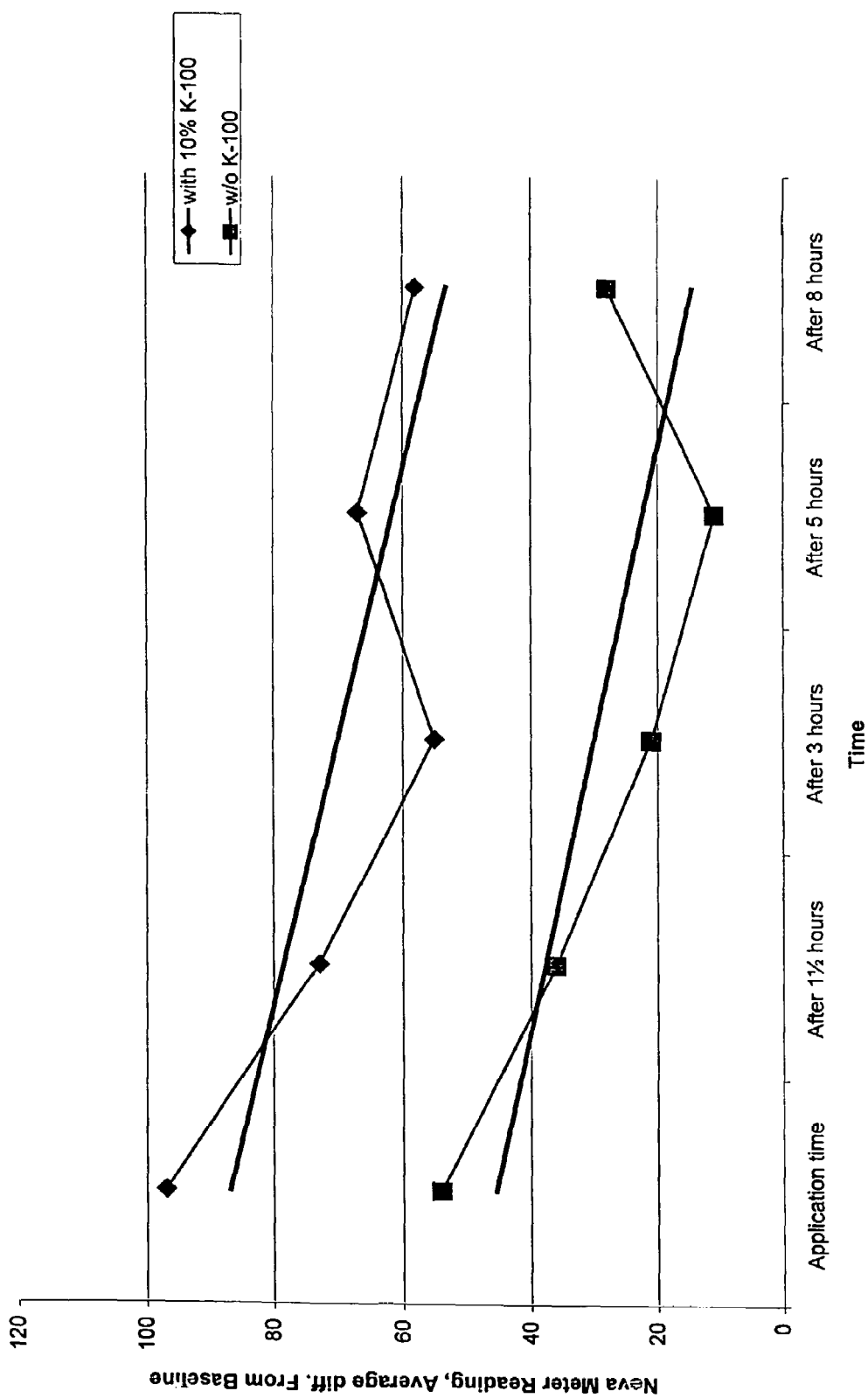
FIG. 1 is a graph of the effects of the Hydrolysate when used with a hydrating lotion.

The present invention is a composition of matter, and method for using the same, which is useful as a topically applied material with several useful inherent properties, such as substantivity. Additionally, the composition is useful for carrying an effective amount of topically applied active materials. More specifically, the composition according the present invention provides a carrying agent for the topical application of materials when superior "lasting" power or substantivity is required. Additionally, the present invention is useful because, among other things, it acts as both an emollient and unique emulsifier and demonstrates substantivity; it has the ability to "fix" many different types of "active" materials, from sunscreens to pharmaceutical preparations to any applied animate or inanimate surface.

For the purposes of this invention, the following definitions should be considered:

"High unsaponifiable materials" or "high unsaponifiable content" oils, waxes, fats, and the like, means compositions that comprises at least 6% by weight of total organic materials that are unsaponifiable and at least 10% by weight of organic materials that are saponifiable (it is possible that the percentage of unsaponifiables may even exceed 95% in some formulations). Therefore, the term includes compositions containing from 6-90% by weight of organics of unsaponifiable materials and 10-94% by weight of saponifiable materials. Examples of bio-based materials with high unsaponifiables are listed in the table below.

| Material | % Unsaponifiables |
|---|---|
| amaranth seed oil | 9% |
| anise seed oil | 7% |

-continued

| Material | % Unsaponifiables |
|---|---|
| avocado seed oil | 57% |
| barley oil | 6% |
| briza oil | 78% |
| buck wheat oil | 7% |
| candelilla wax | 65-75% |
| carnuba wax | 50-55% |
| cassia occidentalis oil (wild coffee) | 7% |
| coffee bean oil | 8% |
| deoiled lecithin | 32% (in Theory) |
| dog fish oil | 16-18% |
| esparto wax | 42-49% |
| oils from fungi and other microorganisms | 6% or greater |
| guayule (plant material extract) | 8-12% |
| jojoba oil | 45% |
| jurinea oil | 40% |
| lanolin | 39% |
| laurel berry oil | 6% |
| olestra(TM) or olean(TM) | 33% (approximation) |
| olive oil concentrate (phytosqualene) | 35-75% |
| olive seed oil | greater than 6% |
| orange roughy oil | 40% |
| ouricury wax | 50-55% |
| quinoa seed oil | 6% |
| rye germ oil | 11% |
| shark liver oil | 60% |
| shea butter | 9-13% |
| sperm whale oil | 36% |
| sugar cane wax | 18-80% |
| sunflower wax | 25-45% |
| tall oil | 9-23% |
| tall oil distillate | 25-33% |
| Vegepure(TM) from wheat grains | 70-90% |
| wheat germ oil | 6% |

"Substantivity" means the tendency of a material to resist being easily removed or the persistence of a treatment on the skin. For example, some sunscreen lotions are substantive because they form a film on the skin that is relatively water-insoluble. This, then, means that substantive materials resist removal or transfer by physical contact, sweating or washing.

Compositions of matter comprising waxes, oils and/or fats (lipids) containing at least 6% by weight unsaponifiable ingredients and at least 10% by weight saponifiable ingredients are subjected to an alkaline hydrolysis reaction to produce a non-foaming, substantive composition with unique surfactant properties that may be used as an active ingredient or as a carrier for application of other active ingredients, e.g., as a carrier base for application of cosmetic, pharmaceutical or other active ingredients. Commercially available bio-based extracts that have high unsaponifiables include, but are not limited to, candelilla wax, camuba wax, jojoba oil, lanolin, lecithin, and shea butter.

The lipid subjected to the process of the invention may be a raw product or it can also undergo various refining and/or modification steps beforehand. Examples of refining processes which may be mentioned are the conventional processes of chemical or physical refining or the more specialized processes for the refining of shea butter, which make it possible in particular to retain or concentrate the maximum amount of unsaponifiable materials, thereafter subjecting such treated materials to the process of the present invention.

The chemical refining which is preferentially used, being applied to the vegetable fats before they are subjected to the process according to the present invention, may be any conventional chemical refining process, in particular any process comprising the following steps:

Step 1: degumming involving insolubilization of the phosphatides with water, generally in the presence of acid, most frequently phosphoric acid, and separation by decantation or centrifugation (continuous process);

Step 2: neutralization of the free fatty acids in the oil by the addition of a sodium hydroxide solution and separation of the soaps formed (called soap stock), most frequently by centrifugation followed by several washes with water, steps 1 and 2 often being performed simultaneously in a continuous process;

Step 3: decolorization with activated bleaching clays at about 100° C. under reduced vacuum, and filtration;

Step 4: deodorization operation necessary for removing the compounds responsible for the odors and flavors of an oil and for producing refined oil. This operation is carried out in an apparatus called a deodorizer, the procedure involving heating of the oil to a high temperature (180°-220° C.) under a vacuum of the order of 4 torr (i.e. about 532 Pa) and a massive injection of steam to strip away impurities.

An alternate physical refining method is understood as a variant of the chemical refining process explained above, the difference being that the neutralization step with sodium hydroxide is not performed and that the removal of the free fatty acids from the oil is effected during the deodorizing step. The refinement conditions selected during this physical refining method may require modification in order to retain the desired properties of the high unsaponifiables selected for use during the procedure for preparation of the present invention.

The extracts used as starting materials for the hydrolysis reaction according to the method of the present invention may be in their raw or refined states. The extracts may also be alkoxylated, polymerized, acetylated, oxidized, reduced, concentrated, hydrogenated, partial hydrogenated, interesterified, double bond modified, randomized, refined, or otherwise modified before the hydrolysis reaction. Since many lipids have low concentrations or fractions (for example 1% or less as discussed above) of unsaponifiables, the present invention encompasses the concentration of low fraction unsaponifiables into higher fractions, i.e., greater than 6%.

The products from the hydrolysis reaction of organic materials that produce unsaponifiables comprises a mixture of: a) polar hydrophilic salts (saponifiables); and b) non-polar, lipophilic materials (unsaponifiables), with the possibility of other materials also present, depending on the source, state and form of the initial reactant.

The composition of materials created by the method according to the present invention are produced by the reaction of aqueous alkali metal hydroxides, e.g., NaOH, LiOH, KOH (the preferred hydroxide), CaOH, MgOH, and the like, with organic lipid compositions, usually plant extracts, oils, fats, or waxes (of the extracts or derivatives of the extracts) where the organic compositions contain a high proportion of unsaponifiable materials (greater than 6%), and preferably as long chain esters.

Jojoba oil may be examined as an example case. Refined jojoba oil contains various proportions of long chain diunsaturated esters. Hydrolysates of refined jojoba oil are nearly a 55:45 mixture of polar hydrophilic long chain salts (alkali salts) and relatively non-polar lipophilic materials (fatty alcohols). The lipophilic fraction is the unsaponifiable materials according to the definition used in this document. The carbon chain lengths of both of these jojoba Hydrolysates include and vary from $C_{18}$ to $C_{24}$ and have ω-9 double bonds as part of each molecule. It has been found that the combination of saponifiable and unsaponifiable fractions of the Hydrolysates according to the present invention has properties that aid in the formulation of cosmetic, pharmaceutical, and other compositions.

The products that result from the hydrolysis of the lipids containing high percentages of unsaponifiable materials, as created during the practice of the present invention, whether used neat, blended, dissolved, dispersed, or emulsified with excipients, solvents, or carriers, can contain and impart useful properties to applied surfaces. These surfaces may be animate surfaces, particularly human skin, plant surfaces, and even the surfaces of inanimate objects, for example objects of wood, fiber, or plastic. The properties can include, but are not limited to, substantivity, emulsification, hydration, and the like.

One of the above-mentioned properties, substantivity, is particularly useful in the field of lipstick, shampoos, conditioners, hair sheens, repellants, attractants, cosmetics, pharmaceuticals, and sunscreens. The property of substantivity is especially beneficial to hair care products, such as "leave in" hair conditioners, where naturally derivatized materials that display substantivity are particularly commercially desirable. Substantivity is also particularly useful with sunscreen, sun block, or tanning formulations, as well as with insect repellants, such as tick, flea and fly repellants, and pesticides. Substantivity may also be beneficial when used on inanimate objects, such as with air fresheners, antibacterial, antimildew, and antifungal agents, flystrips, pesticides, insecticides, insect repellants, herbicides, and the like.

It is theorized that the inclusion of the high levels of unsaponifiable materials in the organic material enables the Hydrolysates according to the present invention to display their unique combination of properties. The precise nature of the unsaponifiable materials within the oils, waxes, fats or other natural extracts is not particularly important (except when a specific property is desired), and each of the variously available natural starting materials may differ significantly in their composition and types of unsaponifiables. For example, Jurinea extracts (e.g., the petroleum ether extracts of Jurinea) may comprise 40% by weight of pentacyclic triterpene alcohols together with their esters (myristate, palmitate, and acetate) as well as $\alpha$-amyrin, $\beta$-amyrin, lupeol, and taraxasterol such as t-taraxasterol (Lipids, K. L. Mikolajczak et al., 1967, Vol. 2, No. 2, pp. 127-132). Briza oil may contain 20% by weight of lipids that are semi-solid, the lipid comprising 49% unsaponifiable digalactosylglycerides, 29% unsaponifiable monogalactosylglycerides and small amounts of conventional saponifiable triglycerides. The predominant fatty acids in the above oils are palmitic acid, oleic acid and linoleic acid (*Lipids, C. R. Smith, Jr. et al., March* 1966, Vol. 1, No. 2, pp. 123-127).

The composition according to the present invention is preferably produced in a batch process using a large steam kettle equipped with a propeller mixer.

A measured quantity of potassium hydroxide pellets are added into the steam kettle with a measured quantity of distilled, deionized, or reverse osmosis purified water. The amount of potassium hydroxide employed in order to completely saponify the free organic acid and/or organic acid ester can accordingly be calculated from the Saponification Value of the starting material and will, in theory, be the stoichiometric amount. In practice, however, it is preferred to employ slightly less than the stoichiometric amount of potassium hydroxide in order to ensure that the Hydrolysates that are formed are not contaminated with unused alkali. The amount of potassium hydroxide employed can be considerably less than the stoichiometric amount, for example, as little as 50% of the stoichiometric amount or less may be used depending upon the desired result. It is to be understood, however, that an amount of potassium hydroxide in excess of the stoichiometric amount, for example, up to 10% more than the stoichiometric amount, can be employed if complete saponification of the organic acid or ester is to be achieved. Excess potassium hydroxide remaining at the end of the reaction may be removed by traditional methods.

The potassium hydroxide pellets and water are stirred together with the propeller mixer until the potassium hydroxide pellets are dissolved. It is important to note, for safety purposes, that heat is generated during this step and the mixture is quite caustic. Individuals nearby should wear gloves, eye and face protection, and clothing protection to avoid burns, both thermal and chemical.

Next, a measured quantity of a refined or derivatized organic material containing a high proportion of unsaponifiables, such as jojoba oil, is gently added to the steam kettle, taking care not to splash the caustic solution contained therein.

The steam kettle is heated to 90-95° C. and held at that temperature range under constant agitation for two hours. At this point, the resultant mixture should be pH tested. If the solution pH is greater than 10.0, continue heating the mixture under constant agitation at 90-95° C. Retest the solution periodically until the pH is 10.0 or less.

Once the pH is 10.0, or less, withdraw a sample for analysis. This sample should be analyzed by such methods as chromatography or by another like or similar method, to show that the reaction has proceeded as desired.

The resultant Hydrolysate may then be diluted by adding a second measure quantity of water, or other diluent, to the steam kettle and stirred with the mixing propeller. Heat should be continuously applied, less than 80° C., until the mixture is homogeneous.

Once homogeneous, the Hydrolysate mixture is cooled to 60° C. while continuing the mixing with the propeller. The Hydrolysate mixture may then be transferred to a holding container and allowed to cool to room temperature before sealing the holding container.

Emulsification is the process of dispersing one material throughout another in separate droplets and, for industry's purposes, effecting a dispersion that will retain its physical characteristics for a period of one to two years at least. The influence on emulsifier type selected for use is related to the ratio of hydrophilic and lipophilic character expressed by the emulsifier with reference to a similar, although reciprocal, character of the oil being emulsified. These two properties have been termed Hydrophilic-Lipophilic Balance (HLB) of the emulsifier and Required HLB of the oil. The HLB system is helpful to the emulsion formulator for the purpose of matching the appropriate emulsifier to a given oil. This matching is usually done experimentally, however, when the HLB of an emulsifier and the HLB requirement of a given oil is known, this experimentation can be greatly reduced. The HLB of the present invention exhibits a unique property of being 3 to 4 HLB numbers wide and in the hydrophilic range. An emulsifier with a wide HLB effective range is advantageous due to the flexiblity inherently imparted by such an emulsifier. The wide HLB effective range of the present invention also provides formulations with an extra margin for dealing with unusual conditions such as pH, heat, cold, and the like, that may be encountered in the normal distribution of cosmetics, pharmaceutical and other bioactive products.

It was noted during an experiment that when a concentrated fly repellant (Purina Horse Spray Concentrate Insecticide) was diluted according to instructions the resulting mixture separated and required reintegration by shaking before use. This separation of components was eliminated by addition of the Hydrolysate according to the present invention, thus demonstrating the unique emulsification property of the Hydrolysate.

Below are described several example uses found for the Hydrolysates according to the present invention.

EXAMPLE 1

Enhanced Skin Hydration

A Nova Meter is an impedance measuring device that is designed and commonly used to provide a non-invasive, objectively reproducible method of measurement for quantifying a biophysical character relative to hydration of the skin. Ten panelists participated in a skin hydration study that utilized a Nova Meter to register and record results. The test was conducted according to the following procedure.

A commercially available skin lotion was purchased and divided equally. Half was used as a control and half was used as a base into which 5% of a jojoba Hydrolysate was incorporated. The jojoba Hydrolysate was prepared according to the method disclosed in this invention. A baseline skin hydration reading was taken with the Nova Meter for each panelist in advance of any lotion application. The control and Hydrolysate containing lotions were applied to different areas of each panelist forearms. The Hydrolysate containing lotion was applied to the right forearm and the control lotion was applied to the left forearm. The Nova Meter was used to take skin hydration readings of the forearm areas to which each participant had applied each lotion. Multiple skin hydration readings were taken and recorded at two-hour intervals after lotion application. The results are illustrated in FIG. 1.

The experiment resulted in a dramatic increase in skin hydration for most all test subjects in the test areas where the Hydrolysate formulation was applied, compared to the test areas of the control formulation. In general, 6 to 10 hours after application, the Hydrolysate lotion formulation demonstrated a 20% to 54% improvement in skin hydration over baseline areas. The Hydrolysate formulation showed a 10% to 47% improvement in skin hydration over skin treated with the control formulation.

EXAMPLE 2

Reduces Dehydration

Two make-up formulas were prepared: a Hydrolysate formulation containing 5% of a Hydrolysate according to the present invention and a control formulation containing an extra 5% water. The 5% water was added to the control formulation to keep the remaining ingredient compositions the same between the two formulations. The control formulation was applied on the left forearm and the Hydrolysate formulation was applied on the right forearm.

Figure 2:
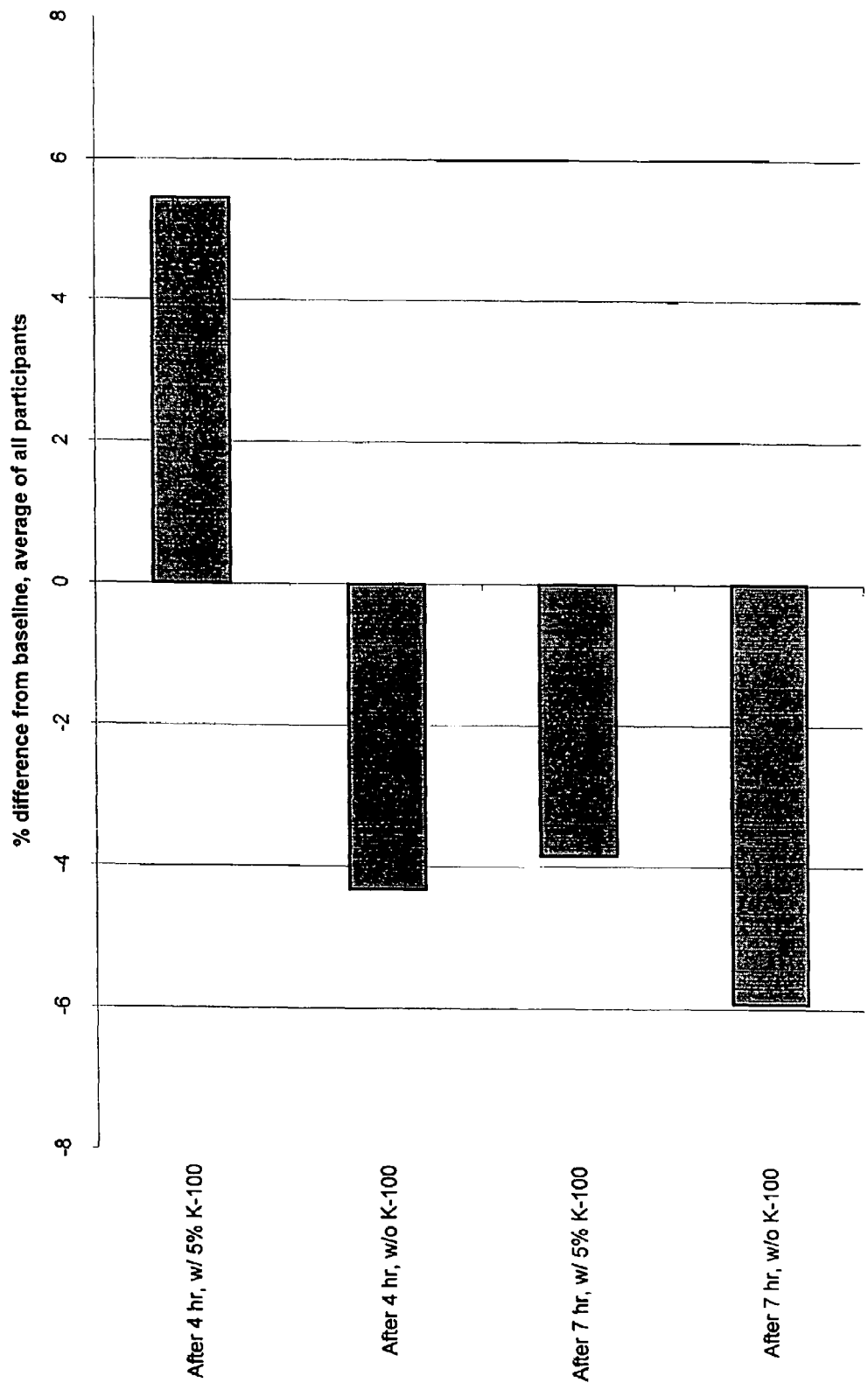
FIG. 2 is a graph of the effects of the Hydrolysate when used with make up.
Figure 3:
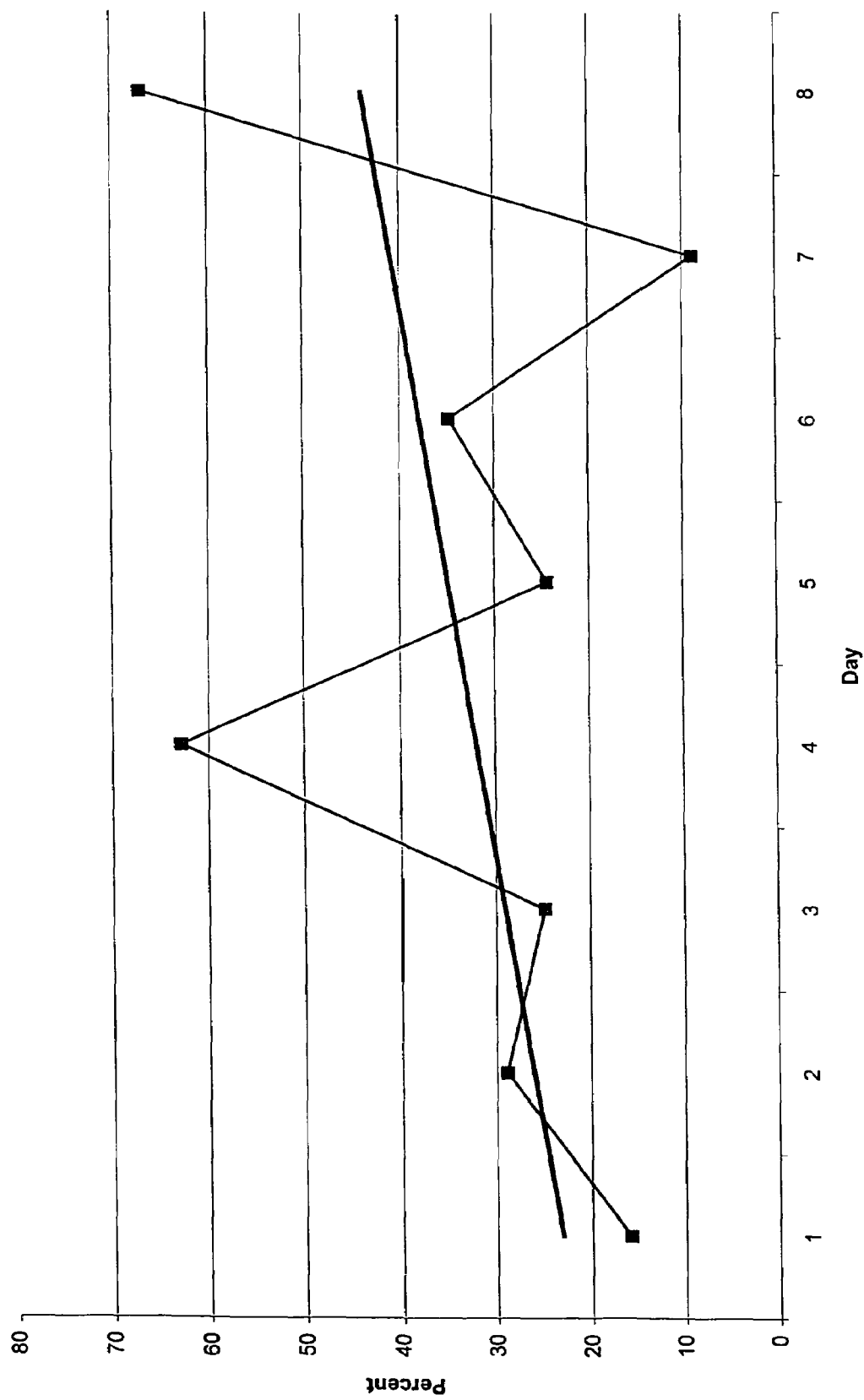
FIG. 3 is an illustration of the average percentage of fly reduction when fly spray incorporates the Hydrolysates according to the present invention.

A Nova Meter was used to take baseline hydration readings of each participant before make-up application and to take hydration readings at intervals of four and seven hours after application of each formulation. The results were averaged for each person using the control and Hydrolysate containing lotions to determine the percent difference in skin hydration from the baseline. The results are shown in FIG. 2.

At four hours after make-up application, the average Nova Meter readings of the participants showed an increase in skin hydration of approximately 5% over baseline on areas to which the Hydrolysate formulation had been applied. A reduction in skin hydration of approximately 4% from baseline was observed on the areas with the control formulation. The difference between the Hydrolysate and control formulations was approximately 9%, with the Hydrolysate formulation showing better hydration properties. In fact, the control formulation showed skin dehydration, which is not unusual for highly pigmented cosmetic formulations such as make-up and lipstick.

At seven hours after application, the average Nova Meter readings of the participants showed a reduction in skin hydration of approximately 4% below baseline on the areas with the Hydrolysate formulation. A reduction in skin hydration of approximately 6% below baseline was observed on the areas with the control formulation. The hydration difference between the two make up formulations after seven hours was approximately 2%, with the Hydrolysate formulation continuing to show better hydration properties than the control formulation. Seven hours were required for the Hydrolysate makeup formulation to approach the drying level to the skin as compared to the control make up formulation.

Therefore, the incorporation of the Hydrolysates according to the present invention into typically drying make-up formations shows improved skin hydration properties compared to formulations not containing the Hydrolysates. In fact, the Hydrolysate formulation appears to hydrate the skin initially, as opposed to the dehydrating effect seen in the control make up formulation.

EXAMPLE 3

Enhanced Performance/Substantivity

Four different products for the treatment of fly abatement with animals, such as horses, were obtained. (Ceratex, Gnat-Away, Solitude, and Aqua-Pel.) Concentrated versions of these products were not available; therefore commercially available dilutions were used.

To each sample, either water or the Hydrolysate according to the present invention was added, to make a 10% Hydrolysate containing solution. All formulations were thoroughly mixed with a stirrer until homogeneous. All formulations were transferred into spray bottles.

Four horses were selected to participate. The left side of each horse was sprayed with the control formulation. The right side of each horse was sprayed with the Hydrolysate formulation. For eight (8) days, the number of flies on each horse's leg prior to re-application of any formulation was determined. With each of the four Hydrolysate formulations, the cumulative effect after eight days demonstrated a significant decrease in fly count. FIGS. 3-7 clearly shows that the Hydrolysate formulation produces a greater decrease in fly count that the control formulation. Thus, the inclusion of the Hydrolysate according to the present invention improves the cumulative performance of the active materials transferred with the Hydrolysate in the commercially available fly abatement products.

The preferred embodiment(s) of the invention is described above in the Detailed Description of the Invention. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A composition comprising jojoba-derived material for providing substantive benefits to the skin of an animal subject, said composition having 10%-55% (wt./wt.) non-polar unsaponifiable fraction and a 45%-90% (wt./wt.) polar hydrophilic salts fraction wherein said non-polar unsaponifiable fraction and said polar hydrophilic salt fraction total 100% of said jojoba-derived material and wherein said jojoba-derived material corresponds to the tandem reaction products of saponification of jojoba oil starting material having about 45% unsaponifiables (wt./wt. of jojoba oil) prior to saponification.

2. The composition of claim 1, wherein:
said jojoba oil starting material is pre-treated prior to saponification; and the method of pre-treatment comprises at least one of: alkoxylation, polymerization, acetylation, oxidation, reduction, concentration, hydrogenation, partial hydrogenation, interesterification, double bond modification, randomization and refinement.

3. The composition of claim 1, wherein said composition comprises an ingredient in at least one of a(n): emollient, conditioner, pigment, dye, pharmaceutical, ultraviolet radiation absorber, physical radiation block, insect repellent, animal repellent, insecticide, pesticide, herbicide, animal attractant, fragrance and hormone.

4. A method of providing substantive benefits to an animal subject, said method comprising the steps of applying the composition of claim 1 to at least one of the hair, skin, scales and feathers of the animal subject.

5. A method of providing substantive benefits to an animal subject, said method comprising the step of applying the composition of claim 2 to at least one of the hair, skin, scales and feathers of the animal subject.

6. A method of providing substantive benefits to an animal subject, said method comprising the step of applying the composition of claim 3 to at least one of the hair, skin, scales, and feathers of the animal subject.

7. A composition comprising jojoba-derived material for providing substantive benefits to the skin of an animal subject, said composition having 10%-55% (wt./wt.) non-polar unsaponifiable fraction and a 45%-90% (wt./wt.) polar hydrophilic salt fraction, wherein said non-polar unsaponifiable fraction and said polar hydrophilic salt fraction total 100% of said jojoba-derived material and wherein said jojoba-derived material corresponds to the tandem reaction products of saponification of jojoba oil starting material having about 45% (wt./wt. of jojoba oil) of long chain carbon material that varies between 18 and 24 carbons in length prior to saponification.

8. The composition of claim 7, wherein:
said jojoba oil starting material is pre-treated prior to saponification; and the method of pre-treatment comprises at least one of: alkoxylation, polymerization, acetylation, oxidation, reduction, concentration, hydrogenation, partial hydrogenation, interesterification, double bond modification, randomization and refinement.

9. The composition of claim 7, wherein said composition comprises an ingredient in at least one of a(n): emollient, conditioner, pigment, dye, pharmaceutical, ultraviolet radiation absorber, physical radiation block, insect repellent, animal repellent, insecticide, pesticide, herbicide, animal attractant, fragrance and hormone.

10. A method of providing substantive benefits to an animal subject, said method comprising the step of applying the composition of claim 7 to at least one of the hair, skin, scales and feathers of the animal subject.

11. A method of providing substantive benefits to an animal subject, said method comprising the step of applying the composition of claim 8 to at least one of the hair, skin, scales and feathers of the animal subject.

12. A method of providing substantive benefits to an animal subject, said method comprising the step of applying the composition of claim 9 to at least one of the hair, skin, scales and feathers of the animal subject.

* * * * *

UNITED STATES PATENT AND TRADEMARK OFFICE
CERTIFICATE OF CORRECTION

| | |
|---|---|
| PATENT NO. | : 7,435,424 B1 |
| APPLICATION NO. | : 09/478071 |
| DATED | : October 14, 2008 |
| INVENTOR(S) | : Copeland et al. |

It is certified that error appears in the above-identified patent and that said Letters Patent is hereby corrected as shown below:

On the face page, in field (57), under "Abstract", in column 2, line 2, delete "Hydrolysates" and insert -- hydrolysates --, therefor.

On the face page, in field (57), under "Abstract", in column 2, line 16, delete "Hydrolysates" and insert -- hydrolysates --, therefor.

On the face page, in field (57), under "Abstract", in column 2, line 22, delete "Hydrolysates" and insert -- hydrolysates --, therefor.

On the face page, at the bottom, in title of graph, delete "Nova Meter" and insert -- Novameter --, therefor.

On Sheet 1 of 7, in Figure 1, in title of line graph, after "Keri" insert -- ® owned by E.R. SQUIBB & SONS LLC --, therefor.

On Sheet 1 of 7, in Figure 1, in title of line graph, delete "Nova Meter" and insert -- Novameter --, therefor.

On Sheet 1 of 7, in Figure 1, in vertical axis name of line graph, delete "Nova Meter" and insert -- Novameter --, therefor.

On Sheet 2 of 7, in Figure 2, in title of line graph, delete "Nova Meter" and insert -- Novameter --, therefor.

Figure 4:
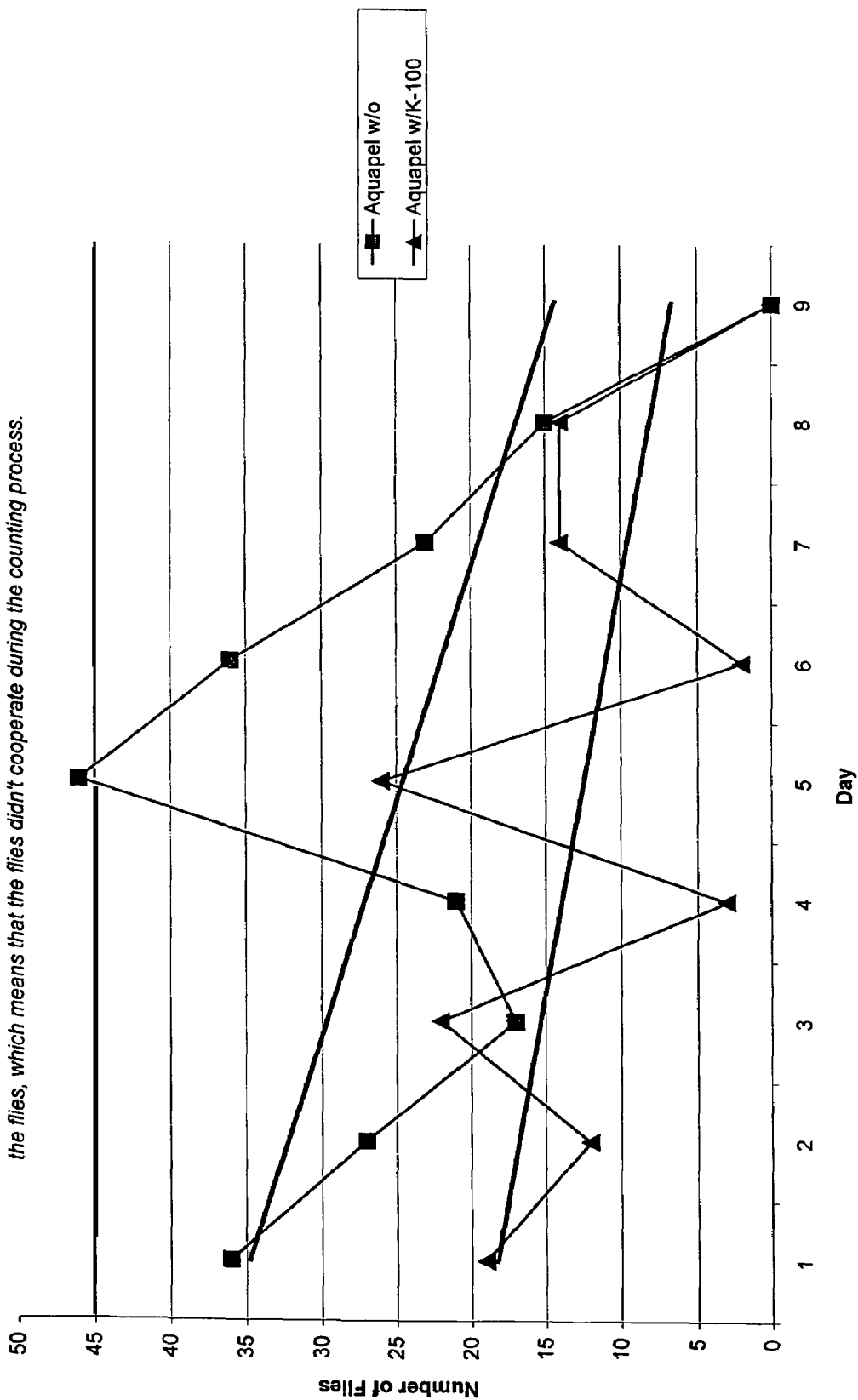
FIG. 4 is the graph of the fly reduction for Aquapel when incorporating the Hydrolysates of the present invention.
Figure 5:
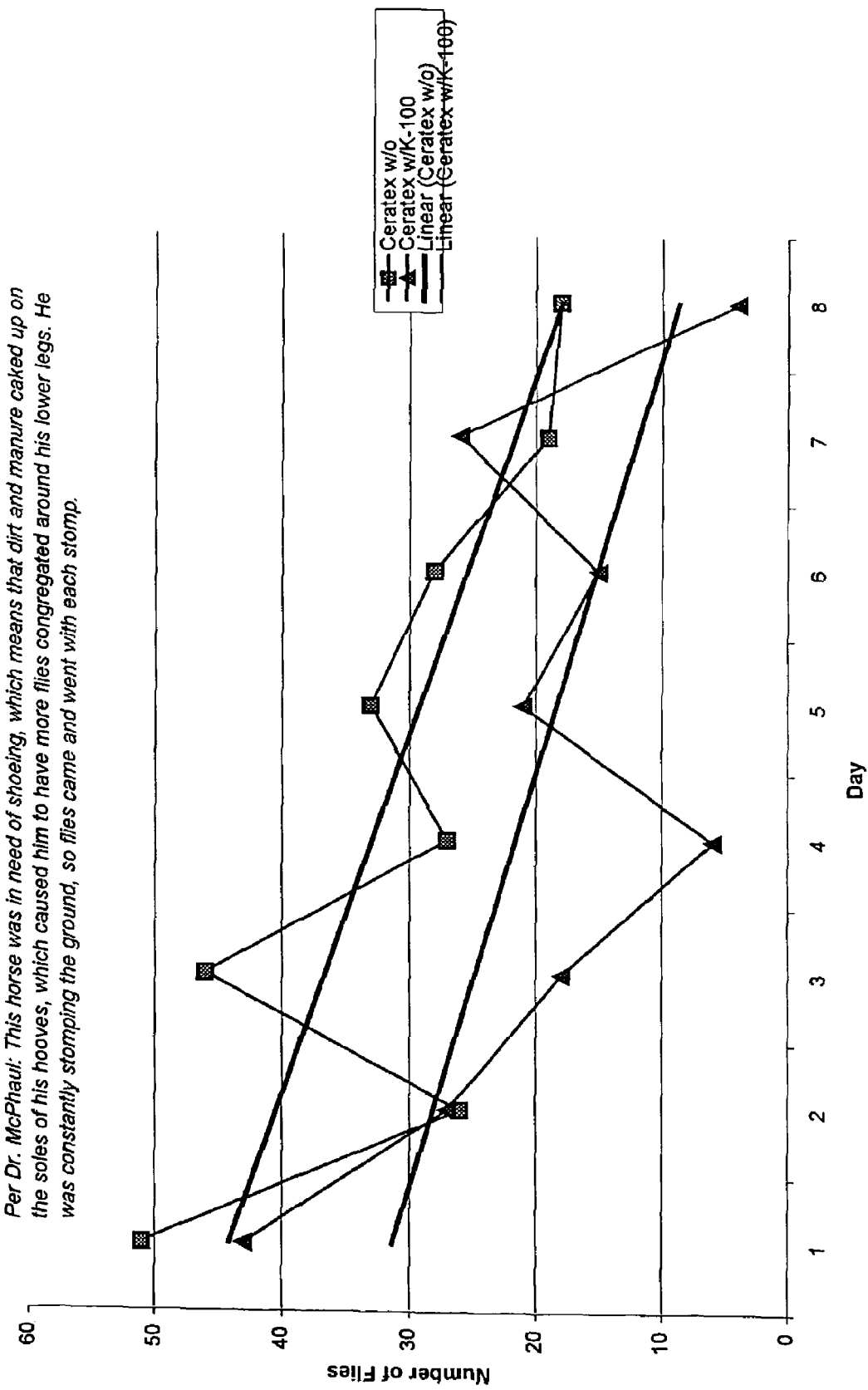
FIG. 5 is the graph of the fly reduction for Ceratex when incorporating the Hydrolysates of the present invention.
Figure 6:
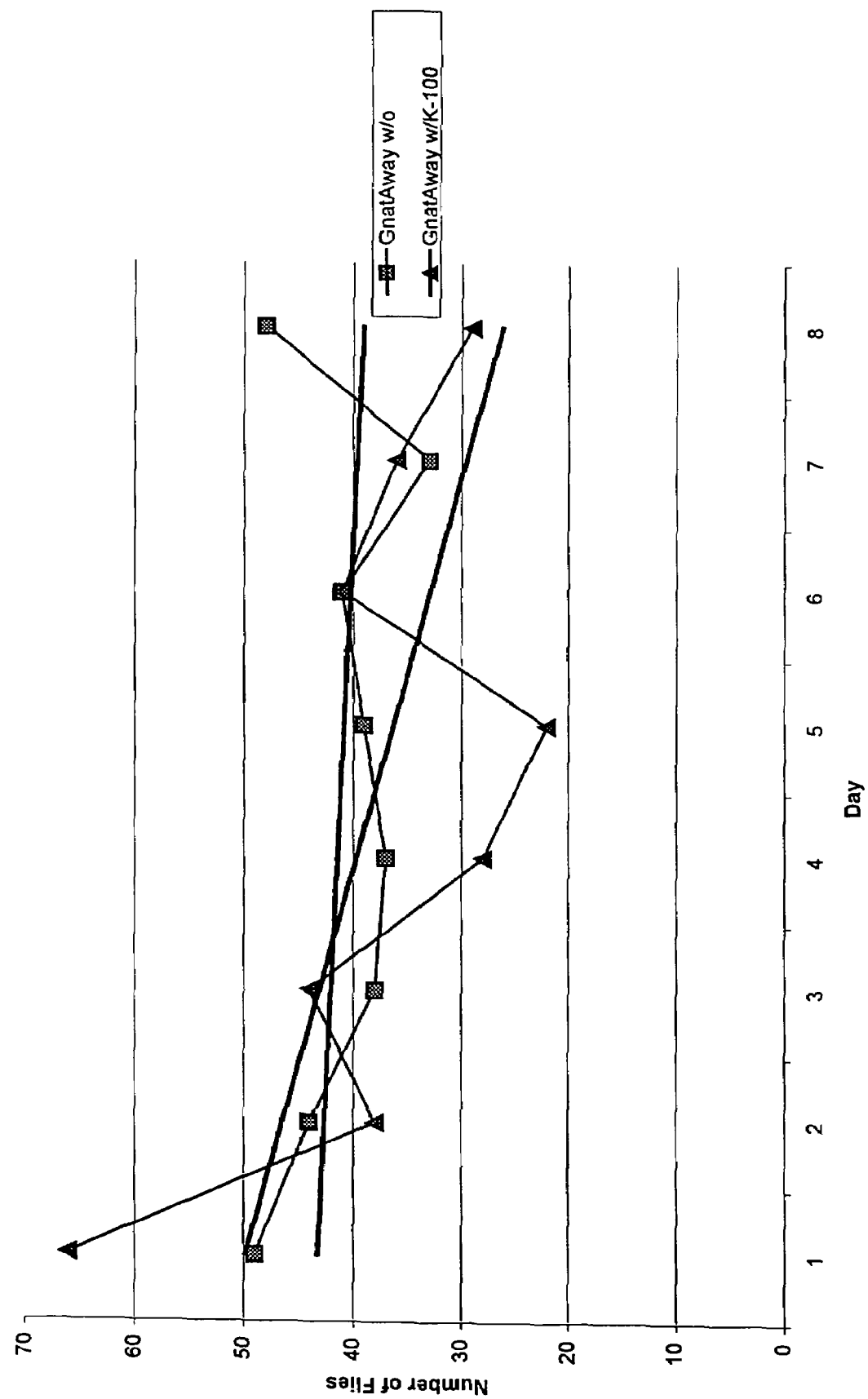
FIG. 6 is the graph of the fly reduction for GnatAway when incorporating the Hydrolysates of the present invention.

On Sheet 4 of 7, in Figure 4, in title of line graph, after "Aquapel" insert -- ® owned by McLaughlin Gormley King Company --.

On Sheet 4 of 7, in Figure 4, in key box of the line graph, line 1, after "Aquapel" insert -- ® owned by McLaughlin Gormley King Company --.

On Sheet 4 of 7, in Figure 4, in key box of the line graph, line 2, after "Aquapel" insert -- ® owned by McLaughlin Gormley King Company --.

On Sheet 7 of 7, in Figure 7, in title of line graph, after "Solitude" insert -- ® owned by Pfizer Inc. --.

On Sheet 7 of 7, in Figure 7, in key box of line graph, line 1, after "Solitude" insert -- ® owned by Pfizer Inc. --.

UNITED STATES PATENT AND TRADEMARK OFFICE
CERTIFICATE OF CORRECTION

| | |
|---|---|
| PATENT NO. | : 7,435,424 B1 |
| APPLICATION NO. | : 09/478071 |
| DATED | : October 14, 2008 |
| INVENTOR(S) | : Copeland et al. |

It is certified that error appears in the above-identified patent and that said Letters Patent is hereby corrected as shown below:

On Sheet 7 of 7, in Figure 7, in key box of line graph, line 2, after "Solitude" insert -- ® owned by Pfizer Inc. --.

In column 1, line 23, delete "Hydrolysates" and insert -- hydrolysates --, therefor.

In column 4, lines 62-63, delete "Hydrolysates" and insert -- hydrolysates --, therefor.

In column 4, line 66, delete "Previously, the" and insert -- The --, therefor.

In column 5, line 5, delete "Hydrolysates" and insert -- hydrolysates --, therefor.

In column 5, line 14, delete "Hydrolysate" and insert -- hydrolysate --, therefor.

In column 5, line 23, delete "contained" and insert -- materials contained --, therefor.

In column 5, line 33, delete "Hydrolysate" and insert -- hydrolysate --, therefor.

In column 5, line 42, delete "Hydrolysates" and insert -- hydrolysates --, therefor.

In column 6, line 16, delete "Hydrolysate" and insert -- hydrolysate --, therefor.

In column 6, line 18, delete "Hydrolysate" and insert -- hydrolysate --, therefor.

In column 6, line 21, delete "Hydrolysates" and insert -- hydrolysates --, therefor.

In column 6, line 23, after "Aquapel" insert -- ® owned by McLaughlin Gormley King Company --.

In column 6, line 24, delete "Hydrolysates" and insert -- hydrolysates --, therefor.

In column 6, line 26, delete "Hydrolysates" and insert -- hydrolysates --, therefor.

In column 6, line 28, delete "Hydrolysates" and insert -- hydrolysates --, therefor.

In column 6, line 29, after "Solitude" insert -- ® owned by Pfizer Inc. --.

In column 6, line 30, delete "Hydrolysates" and insert -- hydrolysates --, therefor.

In column 6, line 44, before "emulsifier" delete "unique".

UNITED STATES PATENT AND TRADEMARK OFFICE
CERTIFICATE OF CORRECTION

PATENT NO. : 7,435,424 B1
APPLICATION NO. : 09/478071
DATED : October 14, 2008
INVENTOR(S) : Copeland et al.

It is certified that error appears in the above-identified patent and that said Letters Patent is hereby corrected as shown below:

In column 7, line 10, delete "cassia" and insert -- Cassia --, therefor.

In column 8, line 2, after "centrifugation" delete "(continuous process)".

In column 8, line 17, after "and" delete "a massive".

In column 8, line 32, delete "partial" and insert -- partially --, therefor.

In column 8, line 47, after "metal" insert -- (or alkali earth metal) --.

In column 8, line 48, delete "CaOH, MgOH" and insert -- $Ca(OH)_2$ and $Mg(OH)_2$ --, therefor.

In column 8, line 56, delete "ofrefinedjojoba" and insert -- of refined jojoba --, therefor.

In column 8, line 61, delete "Hydrolysates" and insert -- hydrolysates --, therefor.

In column 8, line 64, delete "Hydrolysates" and insert -- hydrolysates --, therefor.

In column 9, line 16, delete "derivatized" and insert -- derived --, therefor.

In column 9, line 27, delete "Hydrolysates" and insert -- hydrolysates --, therefor.

In column 9, line 34, delete "Jurinea" and insert -- jurinea --, therefor.

In column 9, line 34, delete "Jurinea" and insert -- jurinea --, therefor.

In column 9, line 55, delete "Saponification" and insert -- saponification --, therefor.

In column 9, line 56, delete "Value" and insert -- value --, therefor.

In column 9, line 59, delete "Hydrolysates" and insert -- hydrolysates --, therefor.

In column 10, line 26, delete "Hydrolysate" and insert -- hydrolysate --, therefor.

In column 10, line 31, delete "Hydrolysate" and insert -- hydrolysate --, therefor.

UNITED STATES PATENT AND TRADEMARK OFFICE
CERTIFICATE OF CORRECTION

PATENT NO. : 7,435,424 B1  
APPLICATION NO. : 09/478071  
DATED : October 14, 2008  
INVENTOR(S) : Copeland et al.

It is certified that error appears in the above-identified patent and that said Letters Patent is hereby corrected as shown below:

In column 10, line 33, delete "Hydrolysate" and insert -- hydrolysate --, therefor.

In column 10, line 37, after "and," delete "for industry's".

In column 10, line 38, before "effecting" delete "purposes,".

In column 10, line 45, delete "Required" and insert -- required --, therefor.

In column 10, line 61, after "Purina" insert -- ® owned by Societe des Produits Nestle S.A. --.

In column 10, line 65, delete "Hydrolysate" and insert -- hydrolysate --, therefor.

In column 10, lines 66-67, delete "Hydrolysate." and insert -- hydrolysate. --, therefor.

In column 11, line 2, delete "Hydrolysates" and insert -- hydrolysates --, therefor.

In column 11, line 8, delete "Nova Meter" and insert -- Novameter (Nova Technology Corporation) <not trademarked> --, therefor.

In column 11, line 13, delete "Nova Meter" and insert -- Novameter --, therefor.

In column 11, line 17, delete "Hydrolysate" and insert -- hydrolysate --, therefor.

In column 11, line 18, delete "Hydrolysate" and insert -- hydrolysate --, therefor.

In column 11, line 20, delete "Nova Meter" and insert -- Novameter --, therefor.

In column 11, line 22, delete "Hydrolysate" and insert -- hydrolysate --, therefor.

In column 11, line 23, delete "Hydrolysate" and insert -- hydrolysate --, therefor.

In column 11, line 25, delete "Nova Meter" and insert -- Novameter --, therefor.

In column 11, line 32, delete "Hydrolysate" and insert -- hydrolysate --, therefor.

In column 11, line 34, delete "Hydrolysate" and insert -- hydrolysate --, therefor.

UNITED STATES PATENT AND TRADEMARK OFFICE
CERTIFICATE OF CORRECTION

PATENT NO.       : 7,435,424 B1
APPLICATION NO.  : 09/478071
DATED            : October 14, 2008
INVENTOR(S)      : Copeland et al.

It is certified that error appears in the above-identified patent and that said Letters Patent is hereby corrected as shown below:

In column 11, line 36, delete "Hydrolysate" and insert -- hydrolysate --, therefor.

In column 11, line 44, delete "Hydrolysate" and insert -- hydrolysate --, therefor.

In column 11, line 45, delete "Hydrolysate" and insert -- hydrolysate --, therefor.

In column 11, line 50, delete "Hydrolysate" and insert -- hydrolysate --, therefor.

In column 11, line 52, delete "Nova Meter" and insert -- Novameter --, therefor.

In column 11, line 56, delete "Hydrolysate" and insert -- hydrolysate --, therefor.

In column 11, lines 59-60, delete "Nova Meter" and insert -- Novameter --, therefor.

In column 11, line 62, delete "Hydrolysate" and insert -- hydrolysate --, therefor.

In column 11, line 65, delete "Hydrolysate" and insert -- hydrolysate --, therefor.

In column 11, line 66, delete "Hydrolysate" and insert -- hydrolysate --, therefor.

In column 12, line 4, delete "Nova Meter" and insert -- Novameter --, therefor.

In column 12, line 7, delete "Hydrolysate" and insert -- hydrolysate --, therefor.

In column 12, line 11, delete "Hydrolysate" and insert -- hydrolysate --, therefor.

In column 12, line 13, delete "Hydrolysate" and insert -- hydrolysate --, therefor.

In column 12, line 16, delete "Hydrolysates" and insert -- hydrolysates --, therefor.

In column 12, line 19, delete "Hydrolysates." and insert -- hydrolysates. --, therefor.

In column 12, line 20, delete "Hydrolysate" and insert -- hydrolysate --, therefor.

In column 12, line 30, delete "Aqua-Pel" and insert -- AquaPel --, therefor.

In column 12, line 33, delete "Hydrolysate" and insert -- hydrolysate --, therefor.

UNITED STATES PATENT AND TRADEMARK OFFICE
CERTIFICATE OF CORRECTION

PATENT NO. : 7,435,424 B1
APPLICATION NO. : 09/478071
DATED : October 14, 2008
INVENTOR(S) : Copeland et al.

It is certified that error appears in the above-identified patent and that said Letters Patent is hereby corrected as shown below:

In column 12, lines 34-35, delete "Hydrolysate" and insert -- hydrolysate --, therefor.

In column 12, line 40, delete "Hydrolysate" and insert -- hydrolysate --, therefor.

In column 12, line 43, delete "Hydrolysate" and insert -- hydrolysate --, therefor.

In column 12, line 46, delete "Hydrolysate" and insert -- hydrolysate --, therefor.

In column 12, line 48, delete "Hydrolysate" and insert -- hydrolysate --, therefor.

In column 12, line 50, delete "Hydrolysate" and insert -- hydrolysate --, therefor.

In column 13, in Claim 2, line 24, in paragraph 2, fix margin formatting.

In column 14, in Claim 8, line 20, in paragraph 8, fix margin formatting.

Signed and Sealed this

Twenty-ninth Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,435,424 B1
APPLICATION NO. : 09/478071
DATED : October 14, 2008
INVENTOR(S) : Copeland et al.

It is certified that error appears in the above-identified patent and that said Letters Patent is hereby corrected as shown below:

Col. 2, line 67, the 2$^{nd}$ instance of "$C_{18:0}$" should be --$C_{18:1}$--.

Col. 5, line 15, "esters" should be --alcohols--.

Signed and Sealed this

First Day of December, 2009

David J. Kappos
*Director of the United States Patent and Trademark Office*